United States Patent [19]

Baroody et al.

[11] Patent Number: 5,733,886
[45] Date of Patent: Mar. 31, 1998

[54] COMPOSITIONS OF CLINDAMYCIN AND BENZOYL PEROXIDE FOR ACNE TREATMENT

[75] Inventors: Lloyd J. Baroody, 1940 Inverness Dr., Scotch Plains, N.J. 07076; Gordon J. Dow, 3868 Lanewood Way, Santa Rosa, Calif. 95404; Debra A. Dow, San Rafael, Calif.; Robert Lathrop, Novato, Calif.

[73] Assignees: Lloyd J. Baroody, Scotch Plains, N.J.; Gordon J. Dow, Santa Rosa, Calif.

[21] Appl. No.: 235,125

[22] Filed: Apr. 28, 1994

Related U.S. Application Data

[63] Continuation of Ser. No. 837,836, Feb. 18, 1992, abandoned.

[51] Int. Cl.[6] .................................................. A61K 31/70
[52] U.S. Cl. .......................... 514/24; 514/859; 514/714
[58] Field of Search .............................. 514/24, 859, 714

[56] References Cited

U.S. PATENT DOCUMENTS

| | | | |
|---|---|---|---|
| 3,535,422 | 10/1970 | Cox et al. | 424/164 |
| 3,969,516 | 7/1976 | Stoughton | 424/181 |
| 4,056,611 | 11/1977 | Young | 424/62 |
| 4,228,163 | 10/1980 | Bliss | 424/240 |
| 4,318,907 | 3/1982 | Kligman et al. | 424/230 |
| 4,323,558 | 4/1982 | Nelson | 424/164 |
| 4,387,107 | 6/1983 | Klein et al. | 424/338 |
| 4,411,893 | 10/1983 | Johnson et al. | 424/181 |
| 4,497,794 | 2/1985 | Klein et al. | 424/81 |
| 4,505,896 | 3/1985 | Bernstein | 514/24 |
| 4,607,101 | 8/1986 | Bernstein | 514/24 |
| 4,692,329 | 9/1987 | Klein et al. | 424/81 |
| 4,731,362 | 3/1988 | Mamashima et al. | 514/202 |
| 4,923,900 | 5/1990 | De Villez | 514/714 |
| 5,446,028 | 8/1995 | Klen et al. | 514/43 |

FOREIGN PATENT DOCUMENTS

| | | |
|---|---|---|
| 0413528 | 2/1991 | European Pat. Off. . |
| 1594314 | 7/1981 | United Kingdom . |
| 2088717 | 6/1982 | United Kingdom . |
| 2150436 | 7/1985 | United Kingdom . |
| WO 91/02533 | 3/1991 | WIPO . |

OTHER PUBLICATIONS

S.B. Tucker et al, "Comparison of Topical Clindamycin Phosphate, Benzoyl Peroxide, and a Combination of the Two for the Treatment of Acne Vulgaris", *British Journal of Dermatology* (1984) 110, 487–492.
Basotherm GmbH, Published Aug., 1991.
Hirschmann (1988) Arch. Dermatol. 124:1691–1700.
Fulton, Jr. et al. (1974) Arch. Dermatol. 110:83–86.

*Primary Examiner*—Elli Peselev
*Attorney, Agent, or Firm*—Weiser & Associates, P.C.

[57] ABSTRACT

Compositions suitable for the treatment of acne by topical application comprise clindamycin and benzoyl peroxide. Kits for preparing the compositions include a solution of clindamycin in a first container and a gel suspension of benzoyl peroxide in a second container. Each component is stored at a pH which promotes stability, and the combination of the two components provides a final composition having a pH which promotes stability and enhances viscosity.

57 Claims, 2 Drawing Sheets

COMPOSITIONS OF CLINDAMYCIN AND BENZOYL PEROXIDE FOR ACNE TREATMENT

This application is a continuation of application Ser. No. 07/837,836 filed Feb. 18, 1992, now abandoned.

BACKGROUND OF THE INVENTION

1. Field of the Invention

The present invention relates generally to compositions and methods for formulating compositions for treatment of acne. More particularly, the present invention relates to compositions comprising benzoyl peroxide and clindamycin for treatment of acne by topical administration.

Acne is a common skin disorder characterized by blackheads, whiteheads, papules, pustules, cysts, and various sized nodules and scars which, in the inflammatory state of the disorder, are contaminated with bacteria such as *Propionibacterium acnes*. The disorder effects skin areas where the sebaceous glands are most active, and bacterial infection can occur in the sebaceous follicles.

A variety of acne treatment methods have been developed, including both systemic and topical administration of antibiotics, topical administration of organic peroxides, particularly benzoyl peroxide, and the like. Of particular interest to the present invention is the topical administration of antibiotic compositions and other active ingredients, such as benzoyl peroxide.

A particularly effective topical composition for the treatment of acne is a combination of erythromycin, a topical antibiotic, and benzoyl peroxide, as described in U.S. Pat. No. 4,497,794. Compositions prepared generally as described in the '794 patent are sold under the tradename Benzamycin® by Dermik Laboratories, Inc., Collegeville, Pa. Benzamycin® is widely prescribed for the treatment of acne and is recognized in some cases to be more effective than treatment with either erythromycin or benzoyl peroxide alone.

The use of products which combine erythromycin and benzoyl peroxide, however, suffers from certain disadvantages. The combination of erythromycin and benzoyl peroxide is unstable and requires refrigeration for storage. The need to refrigerate the product is not only inconvenient for the patient (e.g., it is difficult to continuously refrigerate the product when travelling), the application of a cold medicine to the face is often unpleasant and reduces patient compliance. The need to store the product in a refrigerator can further reduce patient compliance since the product is "hidden away."

The Benzamycin® product suffers from particular formulation problems. In order to prepare the product, a pharmacist must dissolve erythromycin powder in alcohol from the pharmacy stock. Variations in particular alcohols which are available can lead to variability in the compounded product. Moreover, improper compounding by the pharamacist is possible because of the variable dissolution of erythromycin in alcohol resulting in partially dissolved or undissolved aggregates of the drug. As a result, the effective dosage of the compounded product can vary, and some patients have reported that the product sometimes feels "gritty" when applied to the skin.

For these reasons, it would be desirable to provide improved compositions and methods for formulating compositions for the treatment of acne. In particular, it would be desirable to provide products which combine the activity of an antibiotic compound with the activity of benzoyl peroxide, with none or fewer of the disadvantages described above for the combination of erythromycin and benzoyl peroxide. Such compositions should be effective in treating acne, preferably being at least as effective as the use of erythromycin/benzoyl peroxide compositions and more preferably being more effective than erythromycin/benzoyl peroxide compositions. The compositions should also overcome the formulation and stability problems which have been associated with the erythromycin/benzoyl peroxide compositions. That is, the improved compositions should be easy to formulate, should have a smooth consistency after formulation, should be adequately stable, and should have a sufficiently long storage life even without refrigeration.

2. Description of the Background Art

U.S. Pat. No. 4,497,794, discloses compositions combining erythromycin and benzoyl peroxide for the treatment of acne, as described above. Other patents disclosing the combination of erythromycin and benzoyl peroxide for acne treatment and other purposes include U.S. Pat. No. 4,411,893; U.S. Pat. No. 4,692,329; and British Patent No. 1,594,314. The combination of erythromycin with other organic peroxides for the treatment of acne is described in British Patent No. 2,088,717. Other formulations containing benzoyl peroxide for the treatment of acne are described in U.S. Pat. Nos. 3,535,422; 4,056,611; 4,318,907; 4,923,900; 4,387,107; and 4,228,163. Other peroxide formulations for treating acne are described in U.S. Pat. No. 4,607,101. The use of clindamycin and other lincomycin antibiotics for the treatment of acne is described in U.S. Pat. No. 3,969,516. Hirschmann (1988) Arch. Dermatol. 124:1691–1700 and Fulton, Jr., et al. (1974) Arch. Dermatol. 110:83–86 describe the topical use of antibiotics for the treatment of acne.

SUMMARY OF THE INVENTION

The present invention provides novel acne treatment compositions comprising both clindamycin, an antibiotic effective against *Propionibacterium acnes*, and benzoyl peroxide, a keratolytic and desquamative agent which further possesses a broad antibacterial activity. The two agents are combined in a pharmaceutically acceptable fluid carrier, usually a gel, which has been found to provide effective topical treatment of acne. The benzoyl peroxide will be present in the carrier at a concentration from 1% by weight to 20% by weight and the clindamycin will be present at a concentration from 0.2% by weight to 4% by weight. By maintaining the compositions at a pH below 7, the tendency of benzoyl peroxide to oxidize and degrade clindamycin is largely overcome and the product remains stable during storage at room temperature for extended periods, typically several months or longer. Additionally, the compositions of the present invention have been found to remain substantially odor free even after storage at room temperature for extended periods. This is surprising since clindamycin solutions frequently develop a strong offensive odor upon aging. The presence of such an odor is unacceptable in topical formulations which are to be applied to a patient's face.

In a particular aspect of the present invention, the topical compositions are prepared by combining or admixing an aqueous gel suspension of benzoyl peroxide with an aqueous solution of a clindamycin salt or ester. Prior to combination, the two components are maintained individually, each at a pH selected to enhance stability of the component by itself. The individual pH of each component is further selected so that, after combination, the pH of the final admixed product will produce a pH below 7 to provide stability at room temperature during a normal period of use, as described above. More specifically, the pH of the aqueous clindamycin solution is adjusted to a pH in the range from 3.5 to 7, where it is stable and can remain in solution for extended periods. The aqueous suspension of benzoyl peroxide is stored at a pH from 3.5 to 7.0, typically with a gelling agent which has a relatively low viscosity at the storage pH. By combining preselected amounts of the two components, the pH of the combination will be below 7 and the combination will remain stable for several months after admixture at room temperature.

Preparation of the topical compositions by combining two separately maintained components has a number of advantages. While the topical composition itself is stable for a period of months at room temperature, the individual components will be stable for much longer periods, typically for at least two years or longer. Thus, the components may be prepackaged and will have an acceptable shelf life after distribution. The individual components of the present invention are easily formulated prior to use. The benzoyl peroxide is present as a stable suspension and the clindamycin is present as a stable solution, and their combination requires simple mixing without the need to dissolve any dry components. Moreover, there is no need to combine any other ingredients, such as alcohol, from the pharmacist's stock solutions, thus lessening product variability. Additionally, by properly selecting the gelling agent, the initial viscosity of the benzoyl peroxide suspension (at the suspension pH) may be relatively low, while the viscosity of the final product (at the product pH), can be relatively high to provide a desired gel consistency. Thus, the components may be easily combined by a pharmacist to provide a gel having a pleasing consistency and texture for use by the patient.

The present invention further provides a kit for preparation of the topical composition from the individual components. The kit will comprise a first container holding the benzoyl peroxide suspension and a second container holding the aqueous solution of clindamycin salt or ester. In addition, the kit will include instructions to combine the benzoyl peroxide suspension with the clindamycin solution to provide the topical composition. Optionally, the kit may include a disposable mixing spatula for the convenience of the dispensing pharmacist.

The present invention still further comprises methods for treating acne by applying the topical composition to affected areas of the patient's skin.

DESCRIPTION OF THE PREFERRED EMBODIMENT

According to the present invention, topical compositions for the treatment of acne include both clindamycin and benzoyl peroxide present in a fluid carrier or vehicle which is formulated to enhance stability, efficacy, and aesthetic acceptability of the compositions. The clindamycin constituent will be a pharmaceutical grade salt or ester, usually being clindamycin phosphate. Clindamycin phosphate (ester) is preferred over clindamycin hydrochloride (salt) because of its wider compatibility with gelling agents and its more extensive history of topical use. The preparation of suitable clindamycin and equivalent lincomycin compounds are described in U.S. Pat. No. 3,969,516, the disclosure of which is incorporated herein by reference. Pharmaceutical grade clindamycin phosphate is available from commercial suppliers, such as Genzyme Corporation, One Kendall Square, Cambridge, Mass. 02139.

The benzoyl peroxide constituent will be pharmaceutical grade. It may be in the form of a slurry of a finely divided powder, typically having a mean particle size of 35 μm, or lower, or in the form of a hydrous granular material which will have its particle size reduced accordingly during processing according to this invention. Preparation of suitable benzoyl peroxide constituents is well described in the medical and patent literature. See, for example, the U.S. Pat. Nos. 3,535,422; 4,056,611; 4,387,107; and 4,923,900, the disclosures of which are incorporated herein by reference. Suitable benzoyl peroxide raw materials are available from commercial suppliers, such as the Norac Company, Azusa, Calif.

The clindamycin and benzoyl peroxide constituents will be combined in a suitable fluid vehicle or carrier, typically an aqueous carrier, and will preferably be further combined with an aqueous gelling agent, such as neutral, anionic, and cationic polymers, and mixtures thereof. Exemplary polymers include carboxy vinyl polymers, preferably carboxypolymethylene (CAS Registry No. 9007-209) which is commercially available under the tradename Carbopol®, from B.F. Goodrich Chemical Company, Cleveland, Ohio 44138. The most preferred gelling agent is Carbopol®. Other suitable gelling agents include cellulosic polymers, such as gum arabic, gum tragacanth, locust bean gum, guar gum, xanthan gum, cellulose gum, methylcellulose, hydroxyethylcellulose, hydroxypropylcellulose, and hydroxypropylmethylcellulose.

As discussed in more detail below, the gelling agent will usually be initially combined with an aqueous suspension of benzoyl peroxide to form a first component of a two component kit for formulating the topical composition. The gelling agent ideally will be selected to have a reduced viscosity at the pH of the first component and an increased viscosity at the stage of the final product obtained when the two components are combined.

Other ingredients which may optionally be provided in the topical compositions include humectants, such as propylene glycol; solvents, such as alcohol; and anti-microbial preservatives, such as methylparaben and propylparaben. The topical compositions will also include an organic or inorganic base, such as potassium hydroxide, which is used to adjust the pH of the initial components and the final product, as described in more detail hereinbelow.

Table 1 sets forth exemplary formulations for the topical compositions of the present invention and Table 2 sets forth a preferred formulation.

TABLE 1

| Constituent | Weight Percent[1] | |
| --- | --- | --- |
| | Broad Range | Preferred Range |
| Clindamycin | 0.2% to 4% | 1% to 2% |
| Benzoyl peroxide | 1% to 20% | 2.5% to 10% |
| Gelling agent | 0.1% to 5% | 0.5% to 2% |
| Humectant | 0% to 30% | 5% to 15% |
| Antimicrobial preservative | 0% to 2% | 0.1% to 0.5% |

TABLE 1-continued

| Constituent | Weight Percent[1] | |
|---|---|---|
| | Broad Range | Preferred Range |
| Solvent | 0% to 50% | 0% to 20% |
| Buffer, acid or base | pH 4 to <pH 7 | pH 4.5 to pH 5.5 |

[1]Based on total weight in purified water or other suitable fluid carrier.

TABLE 2

| Constituent | Weight Percent[1] |
|---|---|
| Clindamycin | 1.0 |
| Benzoyl peroxide | 5.0 |
| Carboxyl vinyl polymer | 1.25 |
| Propylene glycol | 10.0 |
| Methylparaben | 0.2 |
| Propylparaben | 0.05 |
| pH | 5.0 |

[1]Based on total weight in purified water.

The two-component kit will comprise an aqueous solution of clindamycin having a concentration in the range from 2% to 15% by weight, preferably being in the range from 8% to 12% by weight. It is important that the pH of the solution be maintained within a range from 3.5 to 7, preferably within a range from 6 to 6.5, in order to inhibit precipitation of the clindamycin from the solution, particularly when the solution is exposed to cold temperatures during storage. The pH of an aqueous clindamycin phosphate solution is normally about 3.5, and the pH of the clindamycin component may be increased to within the desired range by the addition of a pharmaceutically acceptable buffer or base, such as potassium hydroxide.

The benzoyl peroxide component of the two-component kit will comprise an aqueous suspension (stable dispersion) of benzoyl peroxide and a concentration in the range from 1% to 20% by weight, preferably in the range from 5% to 10% by weight. The benzoyl peroxide component will also contain the gelling agent, when a gelling agent is present in the combined topical composition. By properly selecting the nature of the gelling agent and the pH of the benzoyl peroxide component, the benzoyl peroxide component itself may be maintained at a relatively low viscosity while the final topical composition (which is at a different pH) will have a relatively higher viscosity. In this way, mixing of the two components to form the topical composition is facilitated (i.e. the lower viscosity of the benzoyl peroxide component makes the combination and mixing with the clindamycin component easier) while the final topical composition can still possess the desired higher viscosity, gel consistency.

Preferably, the viscosity of the benzoyl peroxide component will be below about $9 \times 10^4$ cp, usually being in the range from $5 \times 10^4$ cp to $9 \times 10^4$ cp, more preferably being in the range from $6.5 \times 10^4$ cp to $8.5 \times 10^4$ cp, while the viscosity of the final topical composition product will be in the range from $7 \times 10^4$ cp to $12 \times 10^4$ cp, more preferably being in the range from $8 \times 10^4$ cp to $10 \times 10^4$ cp. These viscosities may be achieved using the polymeric gelling agents, as described above, and a benzoyl peroxide component having a pH in the range from 3.5 to 7.0, preferably in the range from 4.0 to 5.0. The pH may be adjusted by the addition of a pharmaceutically acceptable buffer or base, such as potassium hydroxide. When the benzoyl peroxide component is combined with the clindamycin component, the resulting combined product will have an increased pH resulting in enhanced viscosity within the range set forth above.

The variation of viscosity with pH in a preferred Carbopol® gelling agent is as set forth in Table 3:

TABLE 3

Effect of pH on Viscosity of 0.5 Weight % Solutions of Carbopol® 940

| pH | CP |
|---|---|
| 4.0 | 23,500 |
| 4.5 | 38,500 |
| 5.0 | 48,500 |
| 6.0 | 56,800 |
| 6.5 | 57,800 |
| 7.0 | 57,900 |

Thus, it can be seen that a beneficial increase in viscosity can be achieved by increasing the pH of the final (combined) product relative to the initial pH of the benzoyl peroxide component containing the gelling agent.

The additional constituents, such as the anti-microbial agents, solvents, humectants, and the like, may be present in either the clindamycin component, the benzoyl peroxide component, or both. Such constituents will be present in the individual kit components at concentrations which results in the desired final concentrations in the topical composition, such as set forth in Table 1 above.

The clindamycin component and the benzoyl peroxide component will be stored in separate, sealed containers, such as bottles, jars, vials, ampules, tubes, pouches, and the like, with the two containers usually being packaged together in the form of a kit, usually including instructions on how to admix the final product, and optionally including a mixing spatula. In this way, the kits may be manufactured, distributed, and stored at remote locations where they will be used, typically pharmacies, hospitals, doctor's offices, and the like. The kits will have an extended shelf life, typically being at least a year, usually being at least two years, or longer so long as the clindamycin component and benzoyl peroxide component are formulated as described above.

Figure 1:
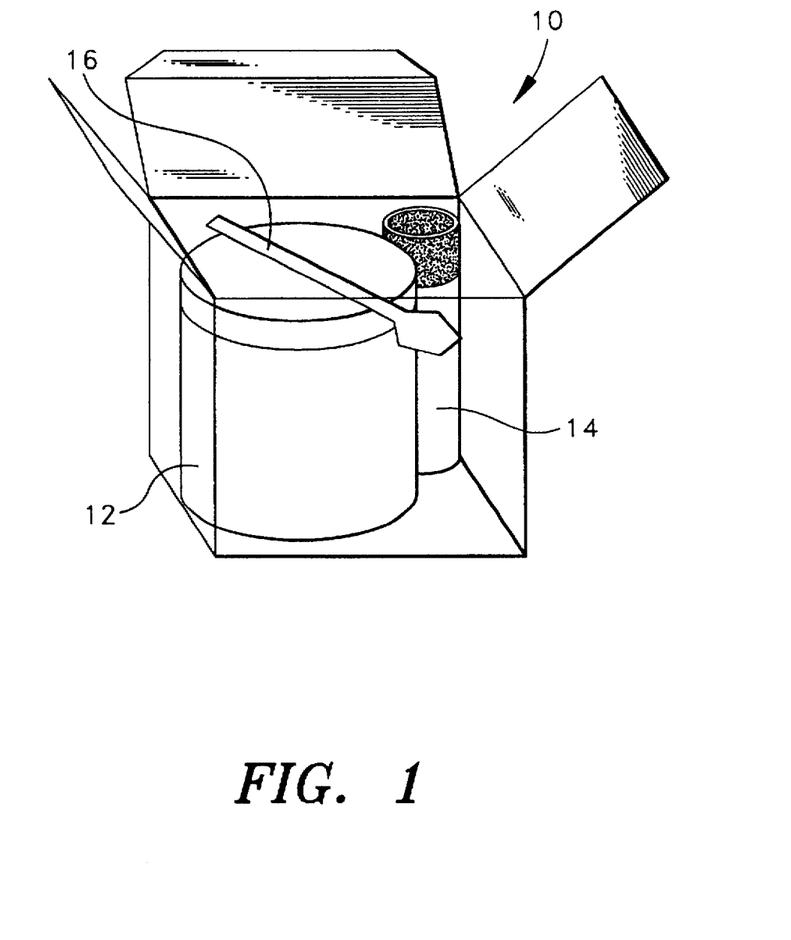
FIG. 1 illustrates a kit according to the present invention.

Conveniently, when packaged together as a kit 10 (FIG. 1), the benzoyl peroxide component will be stored as a low viscosity gel in a jar or other container suitable for mixing. The kit instructions (not illustrated) will call for combining the contents of the clindamycin component container, typically a vial 14, into the benzoyl peroxide container 12 and for subsequently mixing the combination to a uniform consistency. Optionally, the kit 10 may include a disposable spatula 16 for mixing so that the user or pharmacist need not employ any outside materials to formulate the final topical composition.

The relative amounts of the benzoyl peroxide composition and the clindamycin composition in each of the containers will be selected to provide the desired final volume of the topical composition as well as providing the desired final concentrations of the active constituents. Preferably, the ratio of clindamycin solution component to benzoyl peroxide suspension component is in the range of 1 or 2 to 9. Larger proportions of the clindamycin solution can be used, for example, a 1 to 1 ratio of the components, however such a ratio is less preferred because of the increased mixing time required to achieve homogeneity of the admixture. For example, the mixing time for a 1 to 1 ratio of components is twice as long or longer than that for the preferred ratio of about 1 or 2 to 9. The ability to maintain the preferred ratio is at least partly the result of stable incorporation of relatively high concentrations of clindamycin in the clindamycin component at the preferred pH range from 6 to 6.5.

Usually, the total weight of topical composition prepared from a single kit will be in the range from 5 g to 120 g, usually being in the range from 15 g to 45 g. When the clindamycin component is to be added to the benzoyl peroxide component, the weight of the benzoyl peroxide will typically be greater, usually being in the range from 2.5 g to 100 g, more usually being in the range from 12 g to 40 g. The weight of the clindamycin component will usually be in the range from 0.5 g to 60 g, more usually being in the range from 1.5 g to 7 g. The precise weights, volumes, constituent concentrations, pH levels, and the like, are of course all interdependent and must be finally selected to provide the desired characteristics set forth above for the final and mixed product. The determination of the precise formulations for the individual constituents is well within the skill of the art.

The fully formulated (admixed) topical compositions of the present invention may be stored at room temperature and will remain stable, i.e. without substantial loss of efficacy or unacceptable loss of the clindamycin content, for extended periods, typically for at least one month, frequently for two months or longer, and usually for three months or longer.

The topical compositions of the present invention are used to treat acne by applying a thin layer of the composition to the affected area of the skin. Usually, from 0.1 g to 1 g of the topical composition will be applied in a single application, with applications being repeated at least daily, usually being repeated twice daily, and sometimes being repeated at frequency of three times daily or greater.

The following examples are offered by way of illustration, not by way of limitation.

EXPERIMENTAL

Examples 1–4

Aqueous solutions of clindamycin (Genzyme Corp.) were prepared as follows:

|  | Weight Percent | | | |
| --- | --- | --- | --- | --- |
| Component | Ex. 1 | Ex. 2 | Ex. 3 | Ex. 4 |
| Clindamycin Phosphate Ester | 10.58 | 2.38 | 14.28 | 0 |
| Clindamycin Hydrochloride Salt | 0 | 0 | 0 | 7.50 |
| Methylparaben | 0.10 | 0.10 | 0 | 0.10 |
| Propylparaben | 0.02 | 0.02 | 0 | 0.02 |
| Imidurea | 0 | 0 | 0.3 | 0 |
| Potassium Hydroxide, 10% Aqueous Solution (QS) | pH 6.2 | pH 4.5 | pH 6.5 | pH 6.9 |
| Purified Water (QS ad) | 100.00 | 100.00 | 100.00 | 100.00 |

The methylparaben and propylparaben or imidurea were first dissolved in water equivalent to about 75% of the total batch amount. Next, the clindamycin component was added and mixed. After the clindamycin had mostly dissolved, the potassium hydroxide solution was added incrementally (while mixing) to reach the desired pH. Finally, water was added to make the formulation total 100%.

Examples 5–8

Benzoyl peroxide aqueous suspensions were prepared as follows:

|  | Weight Percent | | | |
| --- | --- | --- | --- | --- |
| Component | Ex. 5 | Ex. 6 | Ex. 7 | Ex. 8 |
| Hydrous Benzoyl Peroxide, USP (70%) | 8.67 | 17.34 | 5.00 | 8.67 |
| Imidurea | 0 | 0 | 0.3 | 0 |
| Methylparaben | 0.23 | 0.18 | 0 | 0.20 |
| Propylparaben | 0.06 | 0.06 | 0 | 0.05 |
| Propylene glycol | 11.56 | 7.50 | 0 | 15.00 |
| Carboxy vinyl polymer | 1.45 | 2.0 | 1.0 | 1.45 |
| Potassium Hydroxide, 10% Aqueous Solution (QS) | pH 4.5 | pH 4.3 | pH 4.7 | 0 |
| Trolamine, NF (QS) | 0 | 0 | 0 | 6.5 |
| Purified Water (QS ad) | 100.00 | 100.00 | 100.00 | 100.00 |

The imidurea, methylparaben, propylparaben and/or propylene glycol were first dissolved in an amount of water equivalent to about 65 percent of the total batch amount. The carboxy vinyl polymer was then added slowly while the dispersion was vigorously mixed. While mixing, the potassium hydroxide solution or trolamine was added incrementally to the carboxyl vinyl polymer dispersion to achieve the desired pH. The benzoyl peroxide was levigated with a portion of the carboxy vinyl polymer dispersion and passed through a homogenizer or mill several times until the average particle size was less than 25 microns in diameter. Finally, the benzoyl peroxide dispersion and the remainder of the water were added and mixed into the suspension until homogeneous.

Example 9

Another aqueous suspension of benzoyl peroxide was prepared from pre-micronized benzoyl peroxide as follows:

| Component | Weight Percent |
| --- | --- |
| Hydrous Benzoyl Peroxide, 40%, micronized | 15.17 |
| Propylene Glycol | 11.5 |
| Methylparaben | 0.20 |
| Propylparaben | 0.05 |
| Carboxy Vinyl Polymer | 1.45 |
| Potassium hydroxide, 10% Aqueous Solution (QS) | pH 4.5 |
| Purified Water (QS ad) | 100.00 |

The methylparaben, propylparaben and propylene glycol were dissolved in an amount of water equivalent to about 60 percent of the total batch amount. The carboxy vinyl polymer was then added slowly while the dispersion was vigorously mixed. While mixing, the potassium hydroxide solution was added incrementally to the carboxy vinyl polymer dispersion to achieve the desired pH. The benzoyl peroxide was mixed vigorously with the remaining portion of the water. Finally, the benzoyl peroxide slurry was added to the carboxy vinyl polymer dispersion and mixed until homogeneous.

Example 10

A kit was prepared which included (a) 4 g of the clindamycin aqueous solution of Example 1 in a 4 mL amber glass screw cap vial, (b) 26 g of the benzoyl peroxide aqueous suspension from Example 5 in a 1 ounce wide mouth plastic jar, and (c) a disposable mixing spatula.

The components of the kit were admixed as follows:

1. The entire contents of the vial of clindamycin solution was added to the jar containing the benzoyl peroxide suspension; and 2. Using the disposable plastic spatula, the combination was mixed until the gel became homogeneous (about 1 minute).

An aesthetically pleasing white gel was produced containing about 5.26% benzoyl peroxide and about 1.2% clindamycin (1.4% measured as phosphate).

Example 11

A kit was prepared which included (a) 12 g of the clindamycin aqueous solution of Example 1 in a 15 mL amber glass screw cap vial, (b) 78 g of the benzoyl peroxide aqueous suspension from Example 6 in a 4 ounce wide mouth plastic jar, and (c) a disposable mixing spatula.

The components were admixed as follows:

1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 10.5% benzoyl peroxide and about 1.2% clindamycin (1.4% measured as phosphate).

Example 12

A kit was prepared which included (a) 7.5 g of the clindamycin aqueous solution of Example 2 in an 8 mL amber glass screw cap vial, (b) 7.5 g of the benzoyl peroxide aqueous suspension from Example 6 in a one-half ounce wide mouth plastic jar, and (c) a disposable mixing spatula.

The components were admixed as follows:

1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 6.07% benzoyl peroxide and about 1.0% clindamycin (1.18% measured as phosphate).

Example 13

A kit was prepared which included (a) 8 g of the clindamycin aqueous solution of Example 1 in an 8 mL amber glass screw cap vial, (b) 22 g of the benzoyl peroxide aqueous suspension from Example 7 in a one ounce wide mouth plastic jar, and (c) a disposable mixing spatula.

The components were admixed as follows:

1. The entire contents of the vial of clindamycin solution was added to the jar containing the benzoyl peroxide suspension; and
2. Using the disposable plastic spatula, the combination was mixed until the gel became homogeneous (about 1 minute).

An aesthetically pleasing white gel was produced containing about 2.56% benzoyl peroxide and about 2.3% clindamycin (2.8% measured as phosphate).

Example 14

Aqueous solutions of clindamycin phosphate were tested for chemical and physical stability at various pHs. Table 4 summarizes the clindamycin potency over time at various pH when stored at 40° C. Table 5 summarizes the physical stability over time at various pH when stored at room temperature.

TABLE 4

| Sample No. | pH | Initial | 1 Mo. | 2 Mo. | 3 Mo. |
|---|---|---|---|---|---|
| 1 | 4.95 | 9.75 | 9.91 | — | 9.19 |
| 2 | 5.93 | 11.29 | 11.40 | 11.12 | — |
| 3 | 6.01 | 8.54 | — | — | 7.83 |
| 4 | 6.29 | 8.81 | — | — | 7.88 |

TABLE 5

| Sample No. | pH | Initial | 1 Mo. | 2 Mo. | 3 Mo. |
|---|---|---|---|---|---|
| 1 | 4.95 | clear soln | Heavy ppt. | Heavy ppt. | Heavy ppt. |
| 2 | 5.69 | clear soln | ppt. | ppt. | ppt. |
| 3 | 5.93 | clear soln | clear | clear | clear |
| 4 | 6.01 | clear soln | clear | clear | clear |
| 5 | 6.20 | clear soln | clear | clear | clear |
| 6 | 6.29 | clear soln | clear | clear | clear |

Example 15

The stability of benzoyl peroxide suspension was studied for chemical and physical stability at various pH conditions at 40° C. Table 6 shows the physical stability as well as the assay results for benzoyl peroxide.

TABLE 6

| pH | Test | Initial | 1 Mo. | 2 Mo. | 3 Mo. |
|---|---|---|---|---|---|
| 6.23 | Benzoyl Peroxide Assay (%) | 6.36 | — | 6.42 | 6.06 |
| | Physical Stability | Homogeneous white gel | No change | No change | No change |
| 5.80 | Benzoyl Peroxide Assay (%) | 8.19 | 8.19 | 8.39 | 8.16 |
| | Physical Stability | Homogeneous white gel | No change | No change | No change |
| 4.31 | Benzoyl Peroxide Assay (%) | 6.04 | 6.22 | 6.02 | 5.89 |
| | Physical Stability | Homogeneous white gel | No change | No change | No change |
| 4.22 | Benzoyl Peroxide Assay (%) | 5.91 | 5.96 | — | — |
| | Physical Stability | Homogeneous white gel | No change | No change | No change |

Example 16

Figure 2:
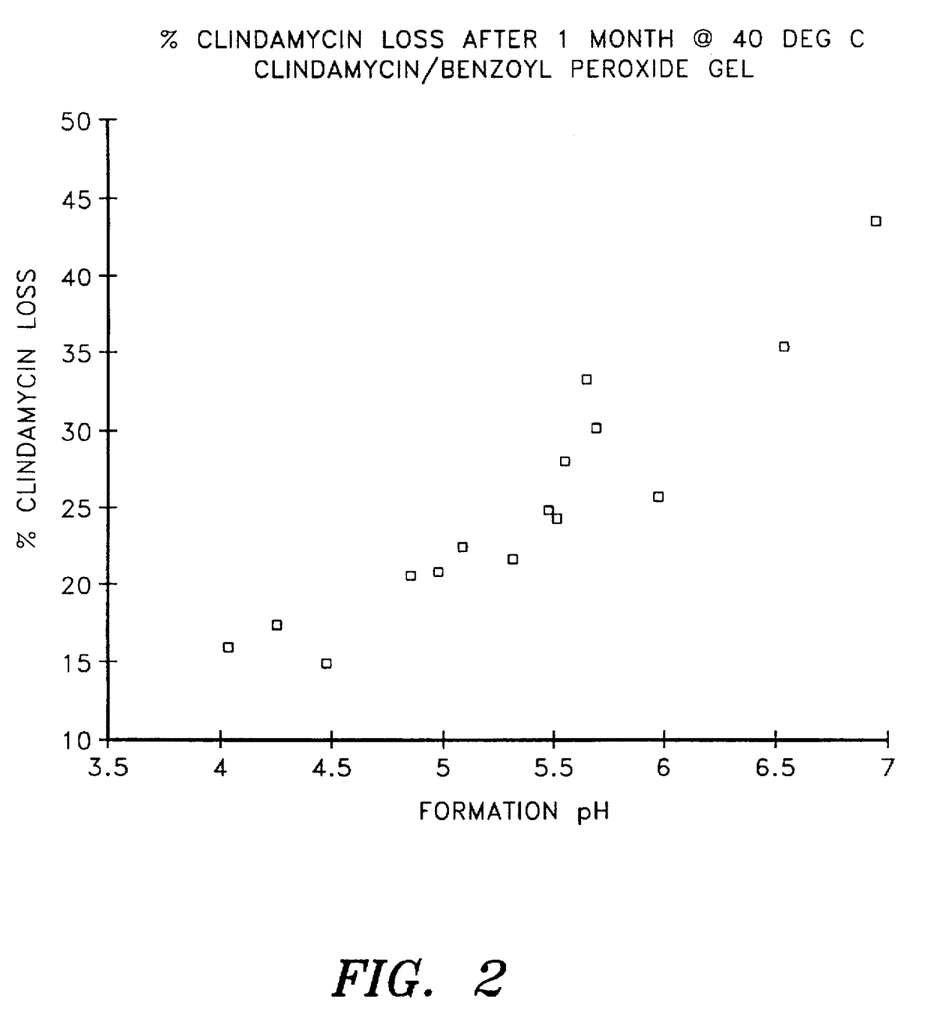
FIG. 2 illustrates the loss of clindamycin in an experimental formulation according to the present invention after admixture of the components and accelerated aging for one month at 40° C.

The chemical stability of the composition containing both clindamycin and benzoyl peroxide, as the kit components are admixed by a pharmacist at the time of dispensing, was studied in an accelerated aging protocol. The effect of pH on stability of clindamycin in the presence of benzoyl peroxide is shown in Table 7 and FIG. 2.

TABLE 7

| | Loss after 1 month | |
|---|---|---|
| Sample | pH | of aging at 40° C. |
| 1 | 6.96 | 43.3 |
| 2 | 6.55 | 35.3 |
| 3 | 5.99 | 25.5 |

TABLE 7-continued

| | Loss after 1 month | |
|---|---|---|
| Sample | pH | of aging at 40° C. |
| 4 | 5.71 | 30.0% |
| 5 | 5.66 | 33.3% |
| 6 | 5.57 | 27.9% |
| 7 | 5.54 | 24.0% |
| 8 | 5.49 | 24.7% |
| 9 | 5.32 | 21.6% |
| 10 | 5.08 | 22.3% |
| 11 | 4.97 | 20.7% |
| 12 | 4.85 | 20.5% |
| 13 | 4.47 | 14.9 |
| 14 | 4.25 | 17.3 |
| 15 | 4.03 | 15.9 |

Example 17

Both clindamycin and benzoyl peroxide in the admixed gel from Example 10 were found to have a shelf-life of be several months at room temperature, as illustrated in Table 8.

TABLE 8

| | Initial | 1 Mo. | 2 Mo. | 3 Mo. |
|---|---|---|---|---|
| Clindamycin | 1.20% | — | 1.08% | 1.01% |
| Benzoyl Peroxide | 5.87% | — | 5.83% | 5.97% |
| Physical Appearance | Pleasant smelling, homogeneous white gel | No change | No change | No change |

Example 18

Five patients with moderate acne vulgaris were treated with the topical gel of Example 10 for six weeks. Each patient applied the gel to his or her face twice daily. Results were evaluated by a dermatologist at weeks 2, 4, and 6, following a baseline pre-treatment evaluation.

In each patient, there was a marked reduction in the number of acne lesions during therapy as set forth in Table 9.

TABLE 9

| | Age (years) | | | | |
|---|---|---|---|---|---|
| | 20 | 16 | 17 | 18 | 22 |
| | | | Gender | | |
| | female | female | male | female | female |
| Number of Inflammatory Lesions Before Treatment | 29 | 14 | 14 | 12 | 14 |
| After Treatment | 6 | 8 | 7 | 7 | 0 |
| Number of Non-Inflammatory Lesions Before Treatment | 26 | 126 | 28 | 41 | 8 |

TABLE 9-continued

| | Age (years) | | | | |
|---|---|---|---|---|---|
| | 20 | 16 | 17 | 18 | 22 |
| | | | Gender | | |
| | female | female | male | female | female |
| After Treatment | 12 | 102 | 14 | 36 | 3 |
| Dermatologist Assessment | E | G | VG | G | E |

E = Excellent
VG = Very Good
G = Good

The dermatologist concluded that the topical gel was highly efficacious in reducing the number of inflammatory and non-inflammatory acne lesions. The dermatologist further concluded that the cosmetic elegance of the topical gel of the present invention (compared to the acne preparations previously used by the patients) likely contributed to the apparent high level of patient compliance in following the twice-a-day protocol regimen, thus contributing to the observed high efficacy. Each of the five patients rated the cosmetic elegance of the topical gel of the present invention as being "excellent" or "good," and every one rated its cosmetic elegance "better" than that of his or her previous or usual topical acne therapy.

Example 19

The material from Example 10 was compared to commercially available Benzamycin® (the commercial product corresponding to U.S. Pat. No. 4,497,794), each product having been admixed according to directions. Pharmaceutical appearance and physical properties were assessed. The composition of the present invention was found to be superior to Benzamycin® in pharmaceutical elegance, as shown below in Table 10.

TABLE 10

| Quality | Topical Gel of Example 10 | Benzamycin® Lot #89449 |
|---|---|---|
| Appearance | Soft, shiny white gel | dull, rubbery white gel |
| Homogeneity | uniform | grainy/syneresis |

Example 20

An experiment was performed to determine the time required by the dispensing pharmacist to compound (admix) the kit in Example 10. For comparison, the same individual compounded Benzamycin® according to the manufacturer's instructions. The invention of the present application provided a significant saving of time for the pharmacist. The results are set forth in Table 11.

TABLE 11

| | Kit of Example 10 | Benzamycin Lot #89449 |
|---|---|---|
| Time to prepare liquid component | 0 sec | 1 min, 15 sec |
| Time to mix components completely (visual end point) | 32 sec | 1 min, 20 sec |
| Total time for pharmacist compounding | 32 sec | 2 min, 35 sec |

Example 21

Thirteen human volunteers participated in a single-blind simultaneous bilateral symmetrical paired comparison of the topical gel of Example 10 and Benzamycin®. The gel from Example 10 was applied to one side of the face in a conventional manner. Benzamycin® was applied to the other side of the face in the same manner. A questionnaire was given to the patients to assess the results. The topical gel of the present invention was highly preferred in each of the properties set forth in Table 12, and therefore represents a distinct improvement over Benzamycin®. Comments made by the volunteers further demonstrate the advantages and improvements. See Table 13.

TABLE 12

| | Composition Preferred (No. of subjects) | | |
|---|---|---|---|
| Cosmetic Property | Topical Gel of Example 10 | Benzamycin Lot #89449 | No Preference |
| Spreadability | 13 | 0 | 0 |
| Feel/texture during application | 13 | 0 | 0 |
| Rub-in properties | 13 | 0 | 0 |
| Odor | 8 | 4 | 1 |
| Skin feel after application | 10 | 1 | 2 |
| Overall preference | 13 | 0 | 0 |

TABLE 13

Descriptive evaluation of cosmetic properties:

| | Typical volunteer comments |
|---|---|
| Benzamycin Lot #89449 | cold, chunky, difficult to spread, sticky, tendency to "ball-up," left residue, and dries slowly. |
| Example 10 | aesthetically pleasant to use, easily spread, rubs in quickly, dries quickly, and is totally absorbed by skin. |

Although the foregoing invention has been described in some detail by way of illustration and example for purposes of clarity of understanding, it will be obvious that certain changes and modifications may be practiced within the scope of the appended claims.

What is claimed is:

1. A topical therapeutic gel composition which is stable at room temperature for at least one month comprising a combination of a pharmaceutically acceptable fluid carrier, and as a first active component, benzoyl peroxide in suspension in a gelling agent, and as a second active component, a solution of a pharmaceutical grade of a clindamycin selected from the group consisting of clindamycin phosphate and clindamycin hydrochloride, the resulting composition having a concentration of benzoyl peroxide from 1% to 20% by weight, a concentration of clindamycin from 0.2% to 4% by weight, a pH of about 4 to less than 7.0 and a viscosity which is higher than the viscosity of the benzoyl peroxide suspension, and the solution of clindamycin before combination with the first active component having an adjusted pH in the range from about 5.9 to 6.9.

2. A kit for preparing a topical therapeutic gel composition which is stable at room temperature for at least one month after mixture of the components of the composition, said kit comprising:
   a first container holding a suspension of benzoyl peroxide in a gelling agent at a pH in the range from about 3.5 to 7.0,
   a second container holding an aqueous solution of a clindamycin selected from the group consisting of clindamycin phosphate and clindamycin hydrochloride at an adjusted pH in the range from about 5.9 to 6.9 and
   instructions associated with the kit to combine the benzoyl peroxide suspension with the clindamycin solution, whereby the resulting composition is a gel having a pH in the range of 4 to less than 7 and having enhanced viscosity in comparison with that of the benzoyl peroxide suspension or the clindamycin solution and the instructions associated with the kit do not call for or require storage of the composition under refrigeration after combination of the benzoyl peroxide suspension and the clindamycin solution.

3. The topical composition of claim 1 wherein the gelling agent is a carboxylated polymer.

4. The topical therapeutic composition of claim 3 wherein the carboxylated polymer is a carboxy vinyl polymer.

5. The topical composition of claim 4 wherein the concentration of the carboxy vinyl polymer in the resulting composition is in the range from 0.1% to 5% by weight.

6. The topical therapeutic composition of claim 4 wherein the pH of the resulting composition is in the range of 4.5 to 5.5.

7. A method for preparing a topical therapeutic gel composition which is stable at room temperature, said method comprising combining (a) an aqueous suspension of benzoyl peroxide initially at a pH of 3.5 to 7.0 in a gelling agent with (b) a stable aqueous solution of a pharmaceutical grade of a clindamycin selected from the group consisting of clindamycin phosphate and clindamycin hydrochloride at an adjusted pH in the range from about 5.9 to 6.9 and selected to provide a pH of the composition in the range from 4.5 to below 7, obtaining the resulting therapeutic gel composition which is stable at room temperature for at least one month, and which has a viscosity greater than that of either the benzoyl peroxide suspension or the clindamycin solution.

8. The topical therapeutic composition of claim 1 wherein the resulting composition has a uniform consistency and has a viscosity in the range from $7 \times 10^4$ cp to $12 \times 10^4$ cp.

9. The topical therapeutic composition of claim 8 wherein the resulting composition has a viscosity in the range from $8 \times 10^4$ cp to $10 \times 10^4$ cp.

10. The topical therapeutic composition of claim 9 which is aqueous.

11. The composition of claim 7 in which after admixing the benzoyl peroxide and the clindamycin 97% of the benzoyl peroxide remains after 3 months when the resulting composition is stored at room temperature.

12. The composition of claim 7 in which after admixing the two components, the pH of the composition is between about 4.03 and about 4.85 and no more than about 20% of the clindamycin is lost after 1 month when the composition is stored at 40° C.

13. The composition of claim 7 wherein the benzoyl peroxide component, prior to combining with the clindamycin component, retains 95% of its original concentration of benzoyl peroxide when the benzoyl peroxide component is stored at 40° C. for 3 months.

14. The composition of claim 7 wherein the clindamycin component, prior to combining with the benzoyl peroxide component, retains 89% of its original concentration of clindamycin when the clindamycin component is stored at 40° C. for 3 months.

15. The kit of claim 2 wherein the gelling agent is a carboxylated polymer.

16. The kit of claim 15 wherein the carboxylated polymer is a carboxy vinyl polymer.

17. A method for treating acne which comprises applying to affected skin areas of a patient a therapeutically effective amount of a gel composition which is stable at room temperature for at least a month, the composition having a pH in the range of about 4 to less than 7, comprising a combination of a pharmaceutically acceptable fluid carrier containing a mixture of a first active component, benzoyl peroxide in suspension in a gelling agent, and as a second active component, a solution of a pharmaceutical grade of a clindamycin selected from the group consisting of clindamycin phosphate and clindamycin hydrochloride, the resulting composition having a concentration of benzoyl peroxide from 1% to 20% by weight, a concentration of clindamycin from 0.2% to 4% by weight, a pH of about 4 to less than 7.0 and a viscosity which is higher than the viscosity of the benzoyl peroxide suspension, and the solution of clindamycin before combination with the first active component having an adjusted pH in the range from about 5.9 to 6.9.

18. The kit of claim 16 wherein the pH of the benzoyl peroxide suspension is in the range from 4.0 to 5.0.

19. The kit of claim 2 wherein the amount of benzoyl peroxide suspension in the first container and the amount of clindamycin solution in the second container are selected to provide a pH of the composition in the range from 4.5 to 5.5 and an increased viscosity when the total contents of each container are combined.

20. The kit of claim 19 wherein the benzoyl peroxide suspension has a pH in the range from 4.0 to 5.0, wherein the clindamycin is in a concentration from 2% to 15% by weight and at a pH from 6.0 to 6.5, and wherein the written instructions for use with the kit provide for combining the benzoyl peroxide suspension with the clindamycin solution at a weight ratio selected to provide a stable gel product having a pH in the range from 4.5 to 5.5 and of enhanced viscosity in comparison with that of the benzoyl peroxide suspension and the clindamycin solution.

21. The kit of claim 20 wherein the volume ratio of clindamycin solution to benzoyl peroxide suspension is in the range from 1 to 9 or 2 to 9.

22. The kit of claim 2 wherein the viscosity of the resulting composition is in the range of $7 \times 10^4$ cp to about $12 \times 10^4$ cp.

23. The kit of claim 22 wherein the viscosity of the resulting composition is in the range from $8 \times 10^4$ cp to $10 \times 10^4$ cp.

24. The kit of claim 23 wherein the amount of benzoyl peroxide suspension is from 2.5 g to 100 g and the amount of clindamycin solution is from 0.5 g to 60 g and the clindamycin is clindamycin phosphate.

25. The kit of claim 2 wherein the viscosity of the benzoyl peroxide in the gelling agent is less than about $9 \times 10^4$ cp.

26. The topical therapeutic composition of claim 1 wherein the clindamycin is clindamycin phosphate.

27. The topical therapeutic composition of claim 26 wherein the adjusted pH of the clindamycin solution is in the range of about 6.0 to 6.5.

28. The topical therapeutic composition of claim 27 wherein the clindamycin solution is chemically stable for two months, measured by the potency of the clindamycin.

29. The kit of claim 22 wherein the clindamycin is clindamycin phosphate.

30. The kit of claim 29 wherein the adjusted pH of the clindamycin solution is in the range of about 6.0 to 6.5.

31. The kit of claim 30 wherein the clindamycin solution is chemically stable for two months, measured by the potency of the clindamycin.

32. The method of preparation of claim 7 wherein the clindamycin is clindamycin phosphate.

33. The method of preparation of claim 32 wherein the adjusted pH of the clindamycin solution is in the range of about 6.0 to 6.5.

34. The method of preparation of claim 33 wherein the clindamycin solution is chemically stable for two months, measured by the potency of the clindamycin.

35. The method of treatment of claim 17 wherein the clindamycin is clindamycin phosphate.

36. The method of treatment of claim 35 wherein the adjusted pH of the clindamycin solution is in the range of about 6.0 to 6.5

37. The method of treatment of claim 36 wherein the clindamycin solution is chemically stable for two months, measured by the potency of the clindamycin.

38. A topical therapeutic gel composition which is stable at room temperature for at least one month comprising a combination of a pharmaceutically acceptable fluid carrier, and as a first active component, benzoyl peroxide in suspension in a gelling agent, and as a second active component, a solution of a pharmaceutical grade of a clindamycin selected from the group consisting of clindamycin phosphate and clindamycin hydrochloride, the resulting composition having a concentration of benzoyl peroxide from 1% to 20% by weight, a concentration of clindamycin from 0.2% to 4% by weight, a pH of about 4 to less than 7.0 and a viscosity which is higher than the viscosity of the benzoyl peroxide suspension, the composition being free of dioctyl sodium sulfosuccinate, and the solution of clindamycin before combination with the first active component having an adjusted pH in the range from about 5.9 to 6.9.

39. A kit for preparing a topical therapeutic gel composition which is stable at room temperature for at least one month after mixture of the components of the composition, the composition being free of dioctyl sodium sulfosuccinate, said kit comprising:

a first container holding a suspension of benzoyl peroxide in a gelling agent at a pH in the range from about 3.5 to 7.0, a second container holding an aqueous solution of a clindamycin selected from the group consisting of clindamycin phosphate and clindamycin hydrochloride at an adjusted pH in the range from about 5.9 to 6.9, and instructions associated with the kit to combine the benzoyl peroxide suspension with the clindamycin solution, whereby the resulting composition is a gel having a pH in the range of 4 to less than 7 and having enhanced viscosity in comparison with that of the benzoyl peroxide suspension or the clindamycin solution and the instructions associated with the kit do not call for or require storage of the composition under refrigeration after combination of the benzoyl peroxide suspension and the clindamycin solution.

40. A method for preparing a topical therapeutic gel composition which is stable at room temperature, the composition being free of dioctyl sodium sulfosuccinate, said method comprising combining (a) an aqueous suspension of benzoyl peroxide initially at a pH of 3.5 to 7.0 in a gelling agent with (b) a stable aqueous solution of a pharmaceutical grade of a clindamycin selected from the group consisting of clindamycin phosphate and clindamycin hydrochloride at an adjusted pH of about 5.9 to 6.9 and selected to provide a pH of the composition in the range from 4.5 to below 7, obtaining the resulting therapeutic gel composition which is stable at room temperature for at least one month, and which has a viscosity greater than that of either the benzoyl peroxide suspension or the clindamycin solution.

41. A method for treating acne which comprises applying to affected skin areas of a patient a therapeutically effective amount of a gel composition which is stable at room temperature for at least a month, the composition having a pH in the range of about 4 to less than 7 comprising a combination of a pharmaceutically acceptable fluid carrier containing a mixture of a first active component, benzoyl peroxide in suspension in a gelling agent, and as a second active component, a solution of a pharmaceutical grade of a clindamycin selected from the group consisting of clindamycin phosphate and clindamycin hydrochloride at an adjusted pH of about 5.9 to 6.9, the resulting composition having a concentration of benzoyl peroxide from 1% to 20% by weight, a concentration of clindamycin from 0.2% to 4% by weight, and a viscosity which is higher than the viscosity of the benzoyl peroxide suspension, the composition being free of dioctyl sodium sulfosuccinate.

42. The topical therapeutic gel composition of claim 38 wherein the solution of clindamycin before combination with the first active component, has an adjusted pH in the range from about 6.0 to 6.5.

43. The topical therapeutic gel composition of claim 42 wherein the clindamycin is clindamycin phosphate.

44. The topical therapeutic gel composition of claim 43 wherein the adjusted pH of the clindamycin solution is in the range of about 6.0 to 6.5.

45. The topical therapeutic gel composition of claim 44 wherein the clindamycin solution is chemically stable for two months, measured by the potency of the clindamycin.

46. The kit for preparing a topical therapeutic gel composition of claim 39 wherein the solution of clindamycin before combination with the first active component, has an adjusted pH in the range from about 6.0 to 6.5.

47. The kit of claim 46 wherein the clindamycin is clindamycin phosphate.

48. The kit of claim 47 wherein the adjusted pH of the clindamycin solution is in the range of about 6.0 to 6.5.

49. The kit of claim 48 wherein the clindamycin solution is chemically stable for two months, measured by the potency of the clindamycin.

50. The method for preparing a topical therapeutic gel composition of claim 40 wherein the solution of clindamycin before combination with the first active component, has an adjusted pH in the range from about 6.0 to 6.5.

51. The method for preparing a topical therapeutic gel composition of claim 50 wherein the clindamycin is clindamycin phosphate.

52. The method for preparing a topical therapeutic gel composition of claim 51 wherein the adjusted pH of the clindamycin solution is in the range of about 6.0 to 6.5.

53. The method for preparing a topical therapeutic gel composition of claim 52 wherein the clindamycin solution is chemically stable for two months, measured by the potency of the clindamycin.

54. The method for treating acne of claim 41 wherein the solution of clindamycin before combination with the first active component, has an adjusted pH in the range from about 6.0 to 6.5.

55. The method of treating acne of claim 54 wherein the clindamycin is clindamycin phosphate.

56. The method of treating acne of claim 55 wherein the adjusted pH of the clindamycin solution is in the range of about 6.0 to 6.5.

57. The method of treating acne of claim 56 wherein the clindamycin solution is chemically stable for two months, measured by the potency of the clindamycin.

* * * * *